US 6,654,637 B2

(12) United States Patent
Rouw et al.

(10) Patent No.: US 6,654,637 B2
(45) Date of Patent: Nov. 25, 2003

(54) METHOD AND SYSTEM FOR VENTRICULAR FUSION PREVENTION

(75) Inventors: Mattias Rouw, Arnhem (NL); Peter Wohlgemuth, Neukirchen (DE)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/844,070

(22) Filed: Apr. 30, 2001

(65) Prior Publication Data
US 2002/0183795 A1 Dec. 5, 2002

(51) Int. Cl.$^7$ .............................................. A61N 1/362
(52) U.S. Cl. ............................................................ 607/7
(58) Field of Search .............................. 607/9, 11, 27, 607/28

(56) References Cited

U.S. PATENT DOCUMENTS

| | | |
|---|---|---|
| 4,316,472 A | 2/1982 | Mirowski et al. |
| 4,365,639 A | 12/1982 | Goldreyer |
| 4,375,817 A | 3/1983 | Engle et al. |
| 4,384,585 A | 5/1983 | Zipes |
| 4,556,063 A | 12/1985 | Thompson et al. |
| 4,577,633 A | 3/1986 | Berkovits et al. |
| 4,726,380 A | 2/1988 | Vollmann |
| 4,727,877 A | 3/1988 | Kallok |
| 4,821,723 A | 4/1989 | Baker et al. |
| 4,825,870 A | 5/1989 | Mann et al. |
| 4,830,006 A | 5/1989 | Haluska et al. |
| 4,880,005 A | 11/1989 | Pless |
| 4,949,719 A | 8/1990 | Pless |
| 5,117,824 A | 6/1992 | Keimel et al. |
| 5,131,388 A | 7/1992 | Pless |
| 5,144,949 A | 9/1992 | Olson |
| 5,158,078 A | 10/1992 | Bennett et al. |
| 5,188,105 A | 2/1993 | Keimel et al. |
| 5,207,218 A | 5/1993 | Carpentier et al. |
| 5,269,298 A | 12/1993 | Adams et al. |
| 5,312,453 A | 5/1994 | Shelton et al. |
| 5,330,507 A | 7/1994 | Schowartz |
| 5,331,966 A | 7/1994 | Bennett et al. |
| 5,534,016 A | 7/1996 | Boute |
| 5,545,186 A | 8/1996 | Olson |
| 5,755,739 A | 5/1998 | Sun et al. |
| 5,800,456 A | 9/1998 | Maeda et al. |
| 5,999,853 A | 12/1999 | Stoop et al. |
| 6,456,881 B1 * | 9/2002 | Bornzin et al. ............... 607/27 |

OTHER PUBLICATIONS

"Onset and Stability for Ventricular Tachyarrhythmia Detection in an Implantable Pacer–Cardioverter–Defibrillator" Olson et al., Computers in Cardiology, Oct. 7–10, 1986, IEEE Computer Society Press, pp. 167–170.

"Automatic Tachycardia Recognition" Arzbaecher et al. PACE, May–Jun. 1984 pp. 541–547.

* cited by examiner

Primary Examiner—George R. Evanisko
(74) Attorney, Agent, or Firm—Girma Wolde-Michael

(57) ABSTRACT

A method and system for ventricular fusion prevention is provided. It is determined whether an atrial sense occurred within a prior wait time and a scheduled ventricular pace is administered if no atrial sense occurred. If an atrial sense occurred and a ventricular sense follows within an additional wait time, the scheduled ventricular pace is canceled to avoid a fusion beat. If an atrial sense occurred and no ventricular sense follows within an additional wait time, the scheduled ventricular pace is administered. In another embodiment, the max AV interval is increased if too many scheduled ventricular paces are canceled to avoid fusion beats.

34 Claims, 9 Drawing Sheets

US 6,654,637 B2

METHOD AND SYSTEM FOR VENTRICULAR FUSION PREVENTION

FIELD OF THE INVENTION

The present invention relates to the field of implanatable medical devices. More particularly, the present invention relates to cardiac pacing systems having venticular fusion prevention.

BACKGROUND

Implantable cardiac pacing systems such as implantable pulse generators (IPGs) are well-known in the art. Implantable cardiac pacing systems deliver a pacing signal to stimulate a heart chamber. The pacing signal is typically delivered by an electrode in the heart chamber. The same electrode is also used to sense electrical activity indicating an intrinsic contraction of the heart chamber. The presence or absence of the sensed contraction, and the timing of the contraction, are used to control the cardiac pacing system for the patient's well being.

The sensing electrodes can only sense electrical activity near the small tip of the electrode, however. Electric activity may have started in the heart chamber, but not yet have reached the sensing electrode. For example, the tip of the ventricular electrode is typically located in the apex of the right ventricle. The ventricular electric wave front may have left the AV node and be on the way to the apex, but the ventricular electrode will not know that any activity has occurred until the electric wave front reaches the sensing site in the apex.

Because the pacing system is unaware that the electric wave front is on its way, it may generate an unnecessary ventricular pace, even though the intrinsic ventricular wavefront would have occurred momentarily. The ventricular pace results in a fusion beat, here defined as a ventricular pace delivered when the ventricle is already contracting by an intrinsic contraction. This type of fusion beat wastes battery energy, reducing the battery life, and interferes with the patient's own intrinsic heart rhythm, which is preferred over the pacing system imposed rhythm.

Fusion pacing could be reduced by providing a ventricular sensing electrode closer to the AV node, but the ventricular electrode is typically located in the apex of the right ventricle. Another signal indicating ventricular activity is the Far Field R-Wave (FFRW) sensed in the atrium. Atrial leads are present in DDD and VDD devices. The Far Field R-Wave (FFRW) is a product of ventricular depolarization sensed in the atrium by the atrial electrode. "Far Field R-Wave Classification by Signal Form," by Westendorp et al., PACE, Vol. 22, June 1999, Part II, P218, page A100, reports that FFRWs originating from intrinsic ventricular contractions can be sensed by the atrial lead up to 25 ms before the ventricular contraction has been sensed by the ventricular lead, depending on the position of the atrial and ventricular leads. In current pacemakers, the FFRW is often blanked with an atrial blanking window to avoid mistaking it for a real atrial event. This atrial blanking window prevents using the FFRW as an early indication of ventricular contraction.

U.S. Pat. No. 5,999,853 to Stoop et al. discloses a dual chamber pacing system for cardiac pacing, preferably a system with a single pass lead providing at least one ring electrode positioned in the patient's atrium, and at least a distal tip electrode for positioning in the patient's right ventricle. At least three signals are selected cyclically for concurrent processing, e.g., the AR signal, atrial ring to can; the VT signal, ventricular tip to can; and RT, atrial ring to ventricular tip. In addition, a second spaced ring can be positioned in each of the atrium and ventricle, for bipolar sensing in each of those heart chambers. In a preferred embodiment, each sensed signal is digitized and processed through the digital signal processor for comparing the patterns of the respective signals, as well as the respective timing of the signals. Based on the pattern and/or timing processing, the concurrent signals are interpreted to represent a P-wave, R-wave or "other," where other may be simply noise, a far field R-wave, or an ectopic beat.

U.S. Pat. No. 5,755,739 to Sun et al. discloses an adaptive and morphological method and system comprising two basic steps. In the first step, an adaptive filtering stage using an R-wave correlated reference (R-Trigger) that removes undesirable R-waves and high amplitude T-waves from the A-EGM signal. The use of R-wave time position sequence or higher order sequence as the reference input signal in the adaptive filter stage significantly enhances the processing speed. In the second step, morphology analysis of the adaptively filtered A-EGM is conducted to detect the P-waves in the adaptive filter output error signal only when atrial channel trigger (P/R-Trigger) signals are detected in the A-EGM. This reduces the amount of time that morphology computation is conducted in the cardiac cycle, thereby reducing computational complexity and allowing real time analysis of the A-EGM in an implantable cardiac stimulator or monitor.

U.S. Pat. No. 5,534,016 to Boute discloses a pacemaker having an algorithm for varying the AV escape interval and detecting when the AV delay is lengthened to the point of evoking a fusion beat, thereby providing an accurate indication of a patient's underlying PR interval without significant loss of pacing capture. By monitoring T-wave detection and drop in amplitude of the evoked T-wave, an algorithm is enabled for optimizing the pacemaker AV delay within a range of values just less than the longest value for obtaining pre-excitation by the delivered pace pulse.

U.S. Pat. No. 4,825,870 to Mann et al. discloses a pacemaker that monitors the heart to detect crosstalk, defined as any signals sensed within a predetermined interval following the atrial stimulation pulse. If crosstalk is detected, the pacemaker follows with a ventricular stimulation pulse at the end of the AVI (which AVI assumes one of two values depending upon whether crosstalk was detected) following the atrial pulse unless a normal ventricular activity is sensed, in which case the ventricular stimulation pulse is inhibited.

U.S. Pat. No. 4,365,639 to Goldreyer discloses a cardiac pacemaker with a single catheter for insertion into a heart through the vascular system. An electrode system for the catheter including a stimulating electrode at the distal end of the catheter for positioning at the apex of the right ventricle, with the stimulating electrode connected to the pulse generating unit of the pacemaker, and sensing electrodes on the catheter spaced from the stimulating electrode for positioning adjacent to the wall of the right atrium for sensing signals generated by the atrial excitation or P-wave, with the P-wave signals connected as input to the pacemaker for determining the timing of the ventricular stimulating pulses. The sensing electrodes are circumferentially equidistant from the stimulating electrode and provide one or more bipolar signals for the pulse generating unit. In alternative configurations, the stimulating electrode and the sensing electrodes are positioned in various locations within the heart to provide other methods of cardiac control.

The most pertinent prior art publications known at the present time are shown in the following table:

TABLE 1

Prior Art Publications

| Publication | Date | Inventor (s) |
| --- | --- | --- |
| Pat. No. 5,999,853 | Dec. 07, 1999 | Stoop et al. |
| Pat. No. 5,755,739 | May 26, 1998 | Sun et al. |
| Pat. No. 5,534,016 | Jul. 09, 1996 | Boute |
| Pat. No. 4,825,870 | May 02, 1989 | Mann et al. |
| Pat. No. 4,365,639 | Dec. 28, 1982 | Goldreyer |
| FFRW Classification | Jun. 00, 1999 | Westendorp et al. |

All publications listed in Table 1 above are hereby incorporated by reference herein in their respective entireties. As those of ordinary skill in the art will appreciate readily upon reading the Summary of the Invention, the Detailed Description of the Preferred Embodiments and the claims set forth below, many of the devices and methods disclosed in the patents of Table 1 may be modified advantageously by using the teachings of the present invention.

SUMMARY OF THE INVENTION

The present invention is therefore directed to providing a system and method for ventricular fusion prevention. The system of the present invention overcomes the problems, disadvantages and limitations of the prior art described above, and provides a more efficient and accurate means of ventricular fusion prevention.

The present invention has certain objects. That is, various embodiments of the present invention provide solutions to one or more problems existing in the prior art ventricular fusion prevention. Those problems include, without limitation: (a) unnecessary battery use from applying a ventricular pace when the intrinsic contraction is already present, (b) ventricular pacing interference with the intrinsic ventricular wavefront, (c) need for ventricular fusion prevention, (d) need for max AV interval adjustment if too many fusion beats are occurring, and (e) uncertainty in electrode placement.

In comparison to known techniques for ventricular fusion prevention, various embodiments of the present invention provide one or more of the following advantages: (a) increased battery life, (b) reduced interference with the intrinsic heart rhythm, and (c) max AV interval adjustment.

Some of the embodiments of the present invention include one or more of the following features: (a) an IMD having ventricular fusion prevention using Far Field R-Wave detection to indicate ventricular contraction, (b) an IMD having ventricular fusion prevention without requiring FFRW form analysis, (c) an IMD having max AV interval adjustment, (d) methods of ventricular fusion prevention, and (e) methods of max AV interval adjustment.

At least some embodiments of the present invention involve starting the fusion beat prevention method when the AV timer has reached the max AV interval and a ventricular pace is scheduled. The activity of the last wait time, defined as a typical time between sensing an intrinsic ventricular contraction at the atrial lead and sensing an intrinsic ventricular contraction at the ventricular lead, is checked to see if atrial activity (Asense) has occurred. If atrial activity was not sensed in the preceding wait time, a ventricular pace is applied immediately because no fusion beat is expected.

If atrial activity was sensed in the preceding wait time, a fusion beat is still possible so the system waits for a ventricular sense (Vsense) to occur or for an additional wait time to elapse. If a ventricular sense occurs, the scheduled ventricular pace is cancelled to avoid a fusion beat. If the wait time elapses without a ventricular sense, a ventricular pace is administered.

Other embodiments of the present invention involve incrementing a fusion beat counter when a ventricular pace is cancelled because a fusion beat would have occurred. When the fusion beat counter reaches a predetermined value, the max AV interval can be increased to give the intrinsic rhythm more chance to occur.

BRIEF DESCRIPTION OF THE DRAWINGS

The above, and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

It is to be understood that the terms "IPG" and "IMD", as employed in the specification and claims hereof, means an implantable medical device capable of delivering electrical stimuli to cardiac tissue, and includes within its scope pacemakers, PCDs, ICDs, etc.

Figure 1:
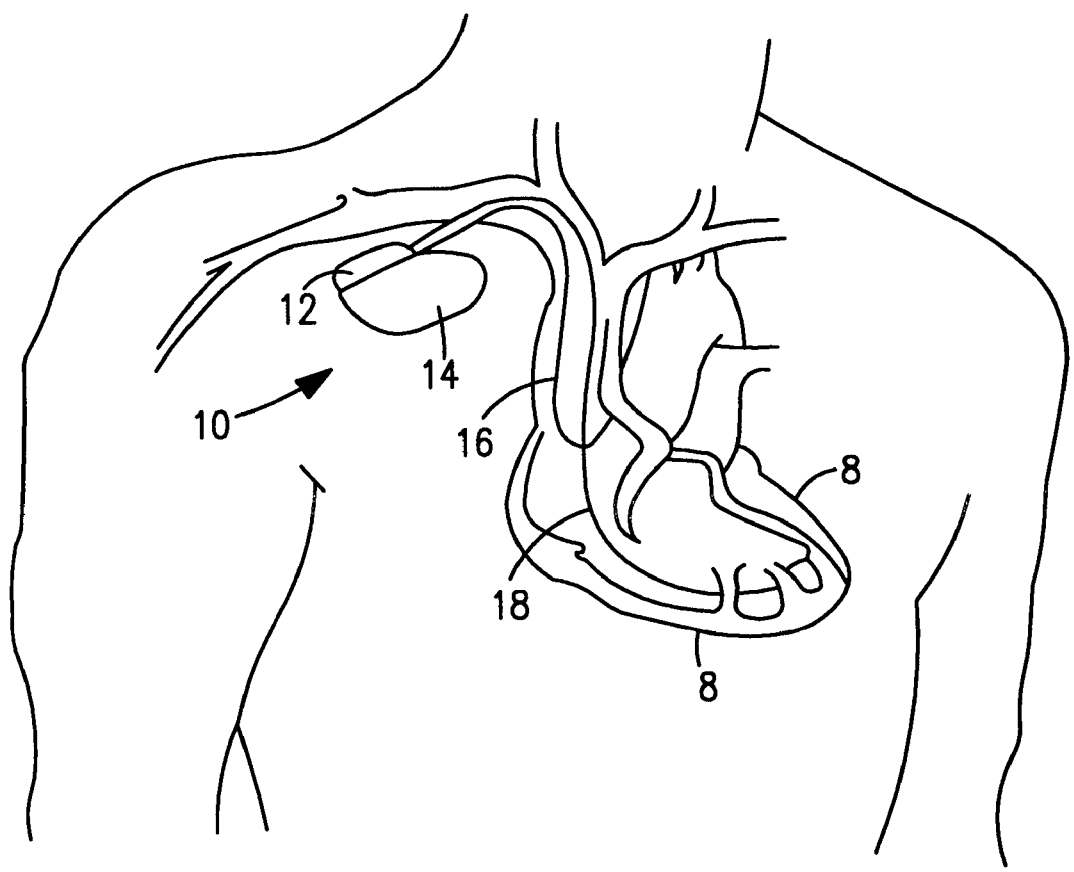
FIG. 1 is a schematic view of one embodiment of an implantable medical device in situ, made in accordance with the present invention.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
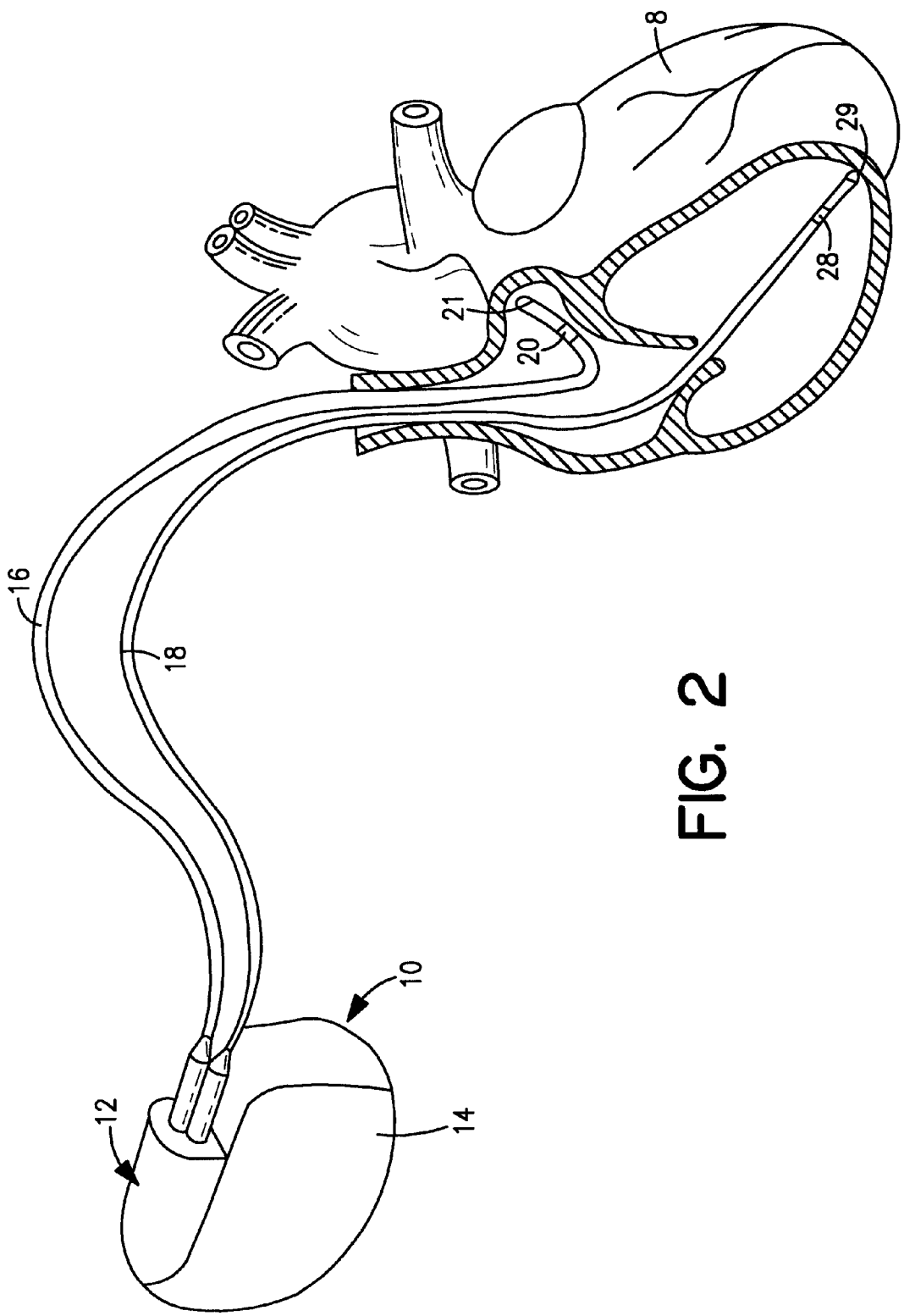
FIG. 2 is another schematic view of an embodiment of the implantable medical device of FIG. 1, made in accordance with the present invention.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
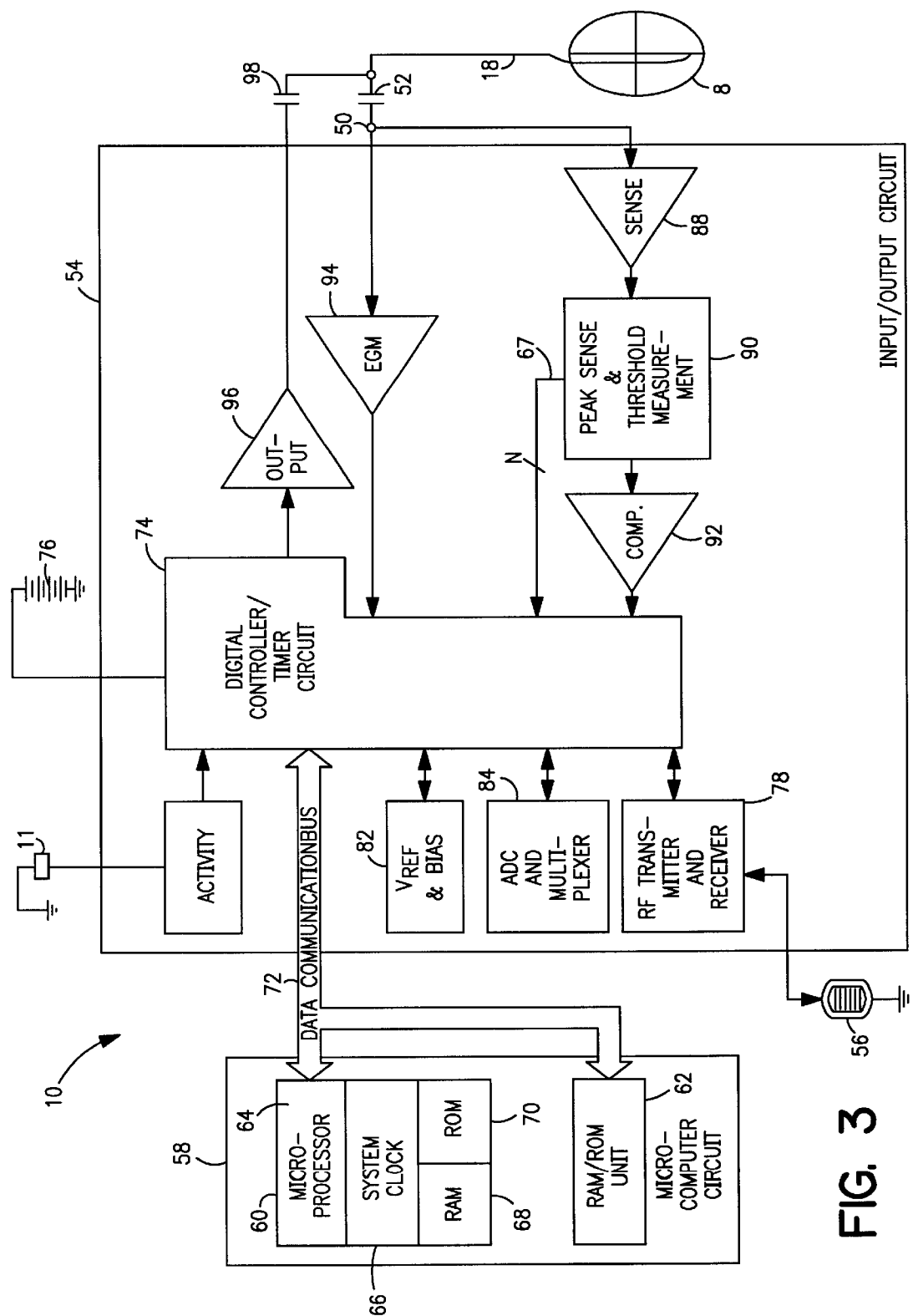
FIG. 3 is a block diagram illustrating components of an embodiment of the implantable medical device of FIG. 1, made in accordance with the present invention.

FIG. 3 shows a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive, including, but not limited to, DDDR, DDIR, VVIR, VOOR and WTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all hereby incorporated by reference herein, each in its respective entirety.

Figure 4:
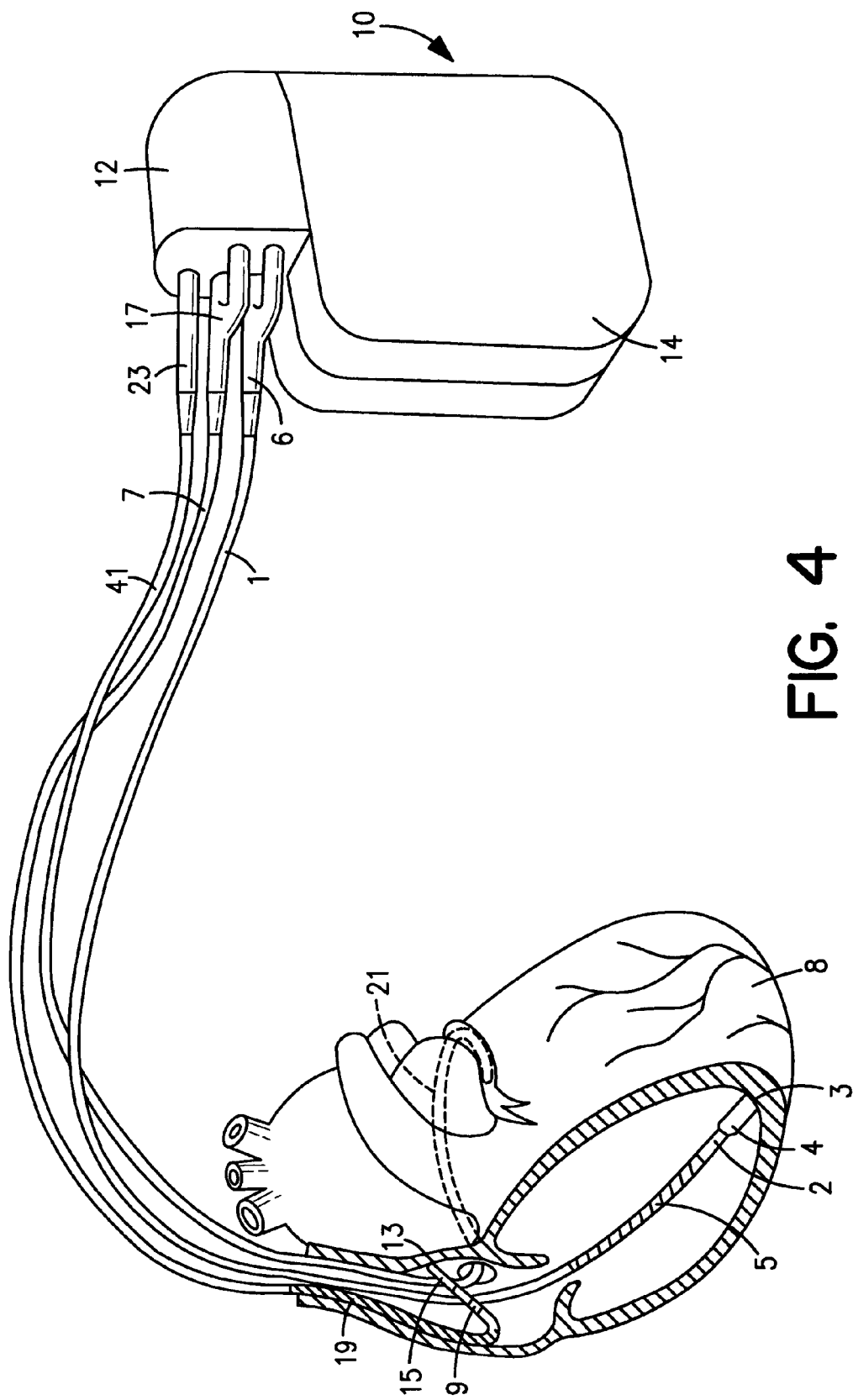
FIG. 4 is a schematic view of another embodiment of an implantable medical device, made in accordance with the present invention.
Figure 5:
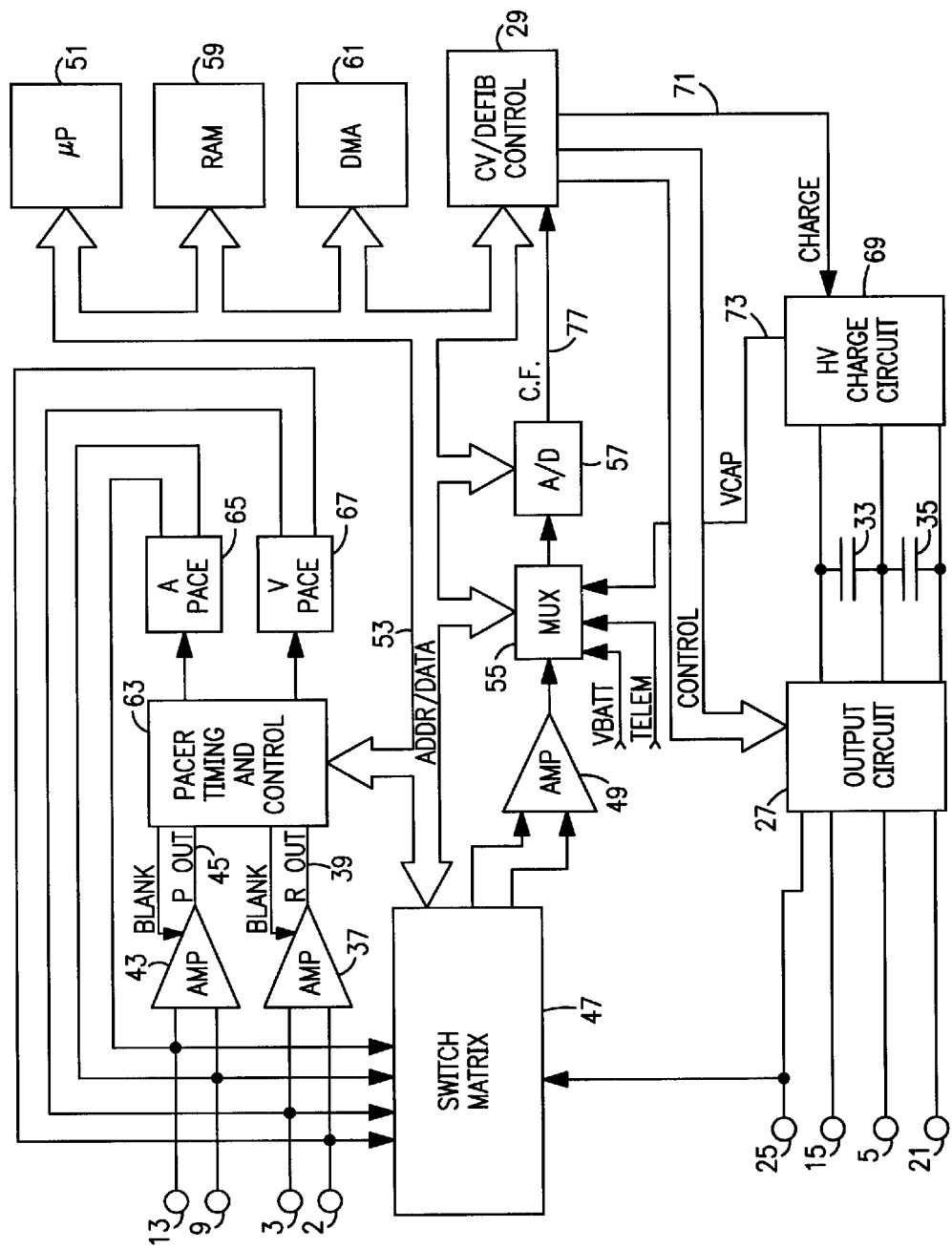
FIG. 5 is a block diagram illustrating components of an embodiment of the implantable medical device of FIG. 4, made in accordance with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R—R intervals, P—P intervals, P–R intervals and R–P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R—R or P–P intervals of an average rate indicative of tachyarrhythmia or an unbroken series of short R—R or P—P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pp. 167–170, also incorporated by reference herein in its entirety. Atrial fibrillation detection methodologies are disclosed in Published PCT Application Serial No. US92/02829, Publication No. WO92/18198, by Adams et al., and in the article "Automatic Tachycardia Recognition", by Arzbaecher et al., published in PACE, May–June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to a cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Figure 6:
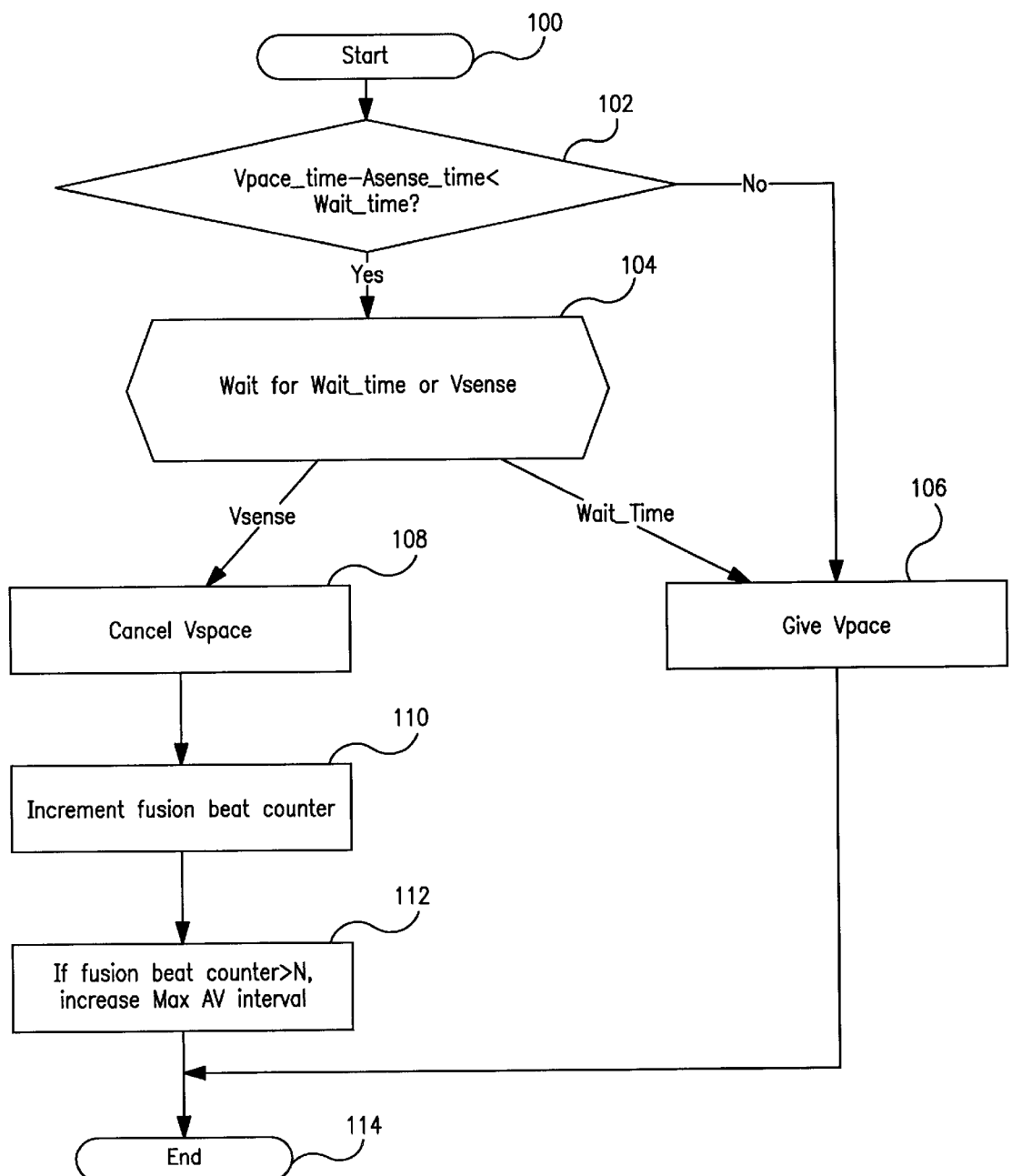
FIG. 6 is a flow chart of a method for ventricular fusion prevention, in accordance with the present invention.

FIG. 6 shows a flow chart of a method for ventricular fusion prevention in accordance with the present invention. An IMD 10 disposed within mammalian heart 8 is programmed to avoid ventricular fusion by using atrial activity to determine if an intrinsic ventricular pulse should be expected. Typically, the atrial activity is a Far Field R-wave (FFRW).

As discussed above, the method of the present invention may be performed under the control of any appropriate computer algorithm stored in a memory or a portion of a memory of microcomputer 58 in IMD 10. Such a computer algorithm may be any program capable of being stored in an electronic medium such as, by way of example only, RAM 68 or ROM 70 of IMD 10, where the contents of RAM 68 and ROM 70 may be accessed and consequently executed by microprocessor 64/microcomputer 58.

Thus an algorithm stored in, for example RAM 68 or ROM 70 of IMD 10 may be used to avoid ventricular fusion. This may be accomplished, for example by using atrial activity, such as FFRW, to determine if an intrinsic ventricular pulse should be expected. The Far Field R-wave (FFRW) is a product of ventricular depolarization sensed in the atrium by the atrial electrode. The FFRW is normally an unwanted atrial sensed signal and is blanked by the input amplifiers of most current pacemaker systems so that it is not detected. This blanking is unnecessary in the next generation of pacemaker systems, however. The new pacemaker system designs use form parameter analysis based on digital signal processing to discriminating between the various signals. Specific form characteristics of the different signals are analyzed to identify the different signals complexes. Since the blanking window is no longer required, the FFRW can be detected and used to identify ventricular activity, if the analysis can be done fast enough. Other possible atrial activities that may indicate an intrinsic ventricular pulse should be expected are retrograde P-waves and nodal P-waves, originating from the AV node.

In one embodiment of the invention, the electrodes may be placed as shown and described above in FIG. 2. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle. The electrodes serve the dual function of supplying cardiac pacing and sensing cardiac activity. The electrodes can only sense electrical activity near the small tip of the electrode, however. Electric activity may have started in the heart chamber, but not yet have reached the sensing electrode. For example, the tip of the ventricular electrode is typically located in the apex of the right ventricle. The ventricular electric wave front may have left the AV node and be on the way to the apex, but the ventricular electrode will not know that any activity has occurred until the electric wave front reaches the sensing site in the apex.

After an atrial pace or intrinsic atrial contraction, it is reasonable to expect that a ventricular contraction is in progress, even if no ventricular sense has yet occurred. A fusion beat may be avoided by checking to see if an atrial sense has occurred in the prior wait time when a ventricular pace is scheduled, then waiting an additional wait time to see if a ventricular sense takes place if there was an atrial sense (because the atrial sense could be a far field R wave). The "wait time" is defined as a typical time between sensing an intrinsic ventricular contraction at the atrial lead and sensing an intrinsic ventricular contraction at the ventricular lead. The wait time depends on placement of the leads and characteristics of the patient's conduction system, and can vary from −25 ms to 120 ms, with an average value of 60 ms, around a ventricular event. The window of −25 to 0 ms before a ventricular event can be used in this invention. "Far Field R-Wave Classification by Signal Form," by Westendorp et al., PACE, Vol. 22, June 1999, Part II, P218, page A100, reports that FFRWs originating from intrinsic ventricular contractions can be sensed by the atrial lead up to 25 ms before the ventricular contraction has been sensed by the ventricular lead, depending on the position of the atrial lead. The wait time can be selected as a typical value for representing the general population or can be selected to fit a particular patient.

Figure 7A:
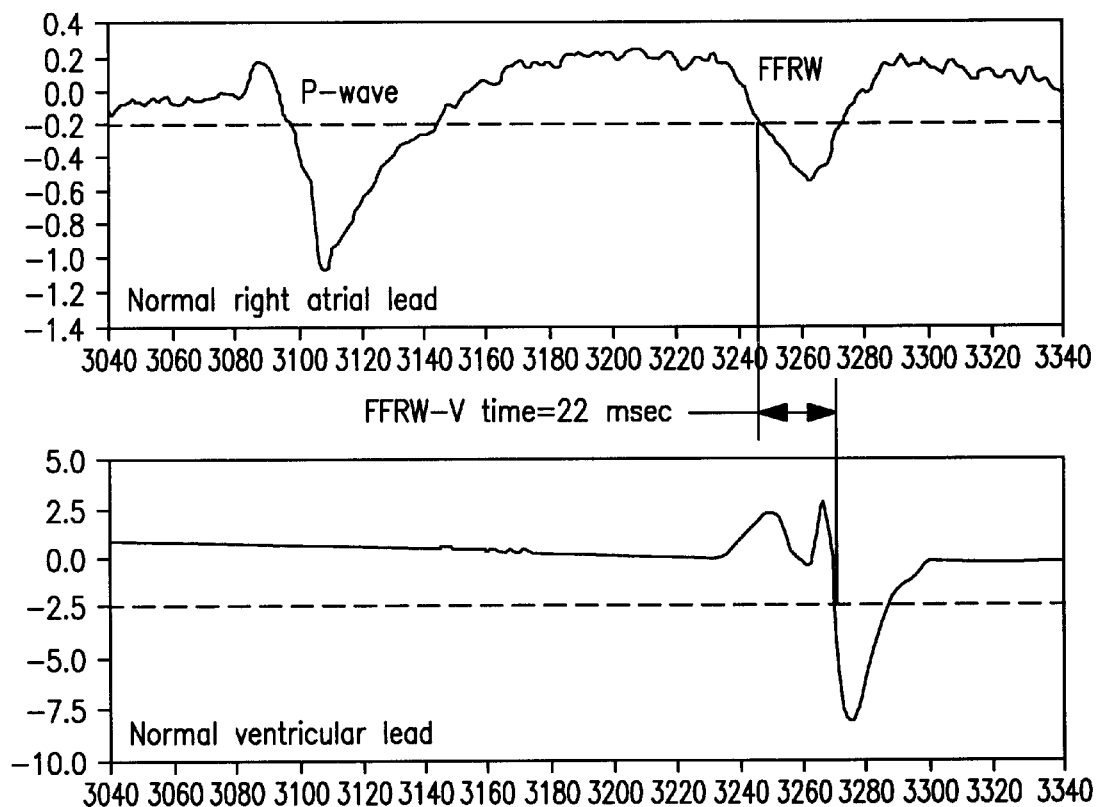
FIGS. 7A & 7B show the time between the FFRW atrial sensing and the ventricular contraction for two cases.
Figure 7B:
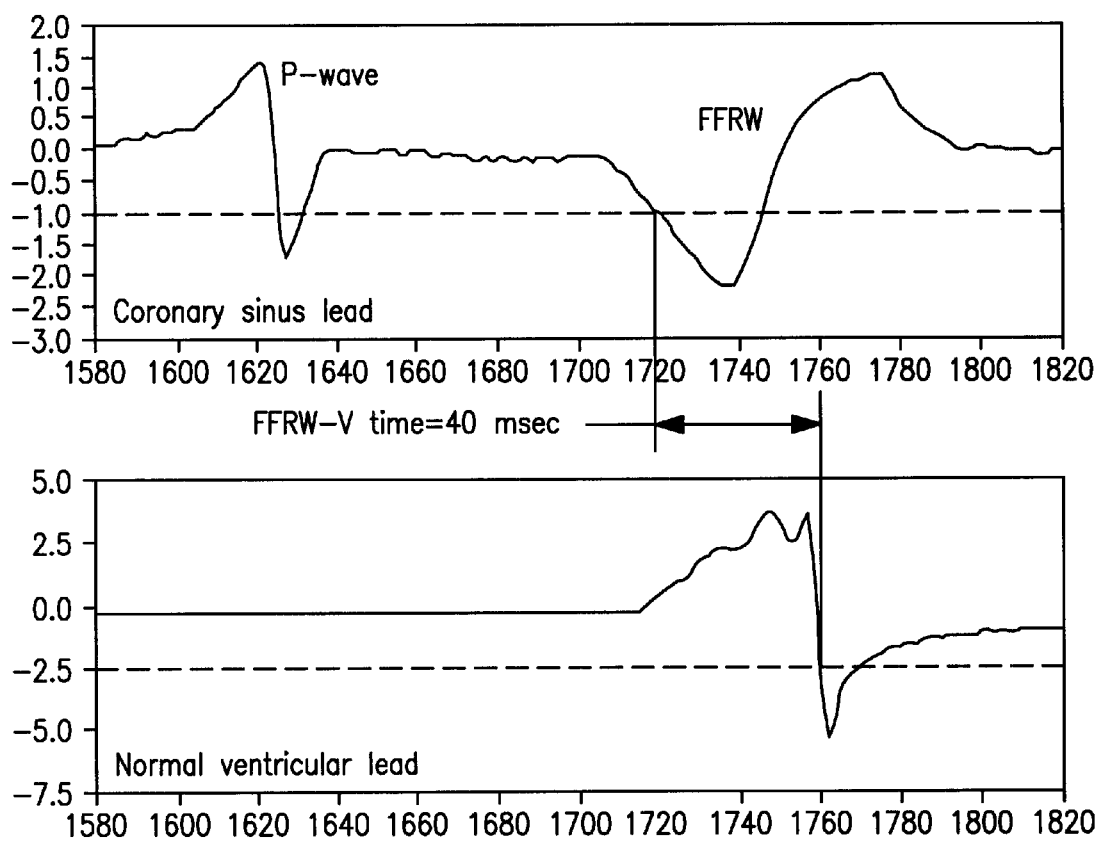

FIGS. 7A & 7B show the time between the FFRW atrial sensing and the ventricular contraction for two cases. The normal right atrial lead in FIG. 7A first detects a P-wave from an atrial contraction. The normal right atrial lead next detects a FFRW. In 22 ms, the normal ventricular lead detects the ventricular contraction. Similarly, the coronary sinus lead in FIG. 7B first detects a P-wave from an atrial contraction. The coronary sinus lead next detects a FFRW. In 40 ms, the normal ventricular lead detects the ventricular contraction. These cases illustrate that a fusion beat can be avoided by delaying a scheduled ventricular pace if atrial activity occurred within the prior wait time to see if a ventricular contraction occurs within the following wait time.

It is important to note that FIGS. 7A and 7B illustrates merely one embodiment of the present invention, and is not intended the limit the scope of the present disclosure or claims to that which is presented therein. Upon reading the specification and reviewing the drawings hereof, it will become immediately obvious to those skilled in the art that myriad other embodiments of the present invention are possible, and that such embodiments are contemplated and fall within the scope of the presently claimed invention.

The fusion beat prevention method starts at block 100 of FIG. 6. Typically, the IMD 10 will enter the fusion beat prevention method at the end of the AV delay, that is, when the AV timer has reached the max AV interval and a ventricular pace is scheduled.

As seen in FIG. 6, the max AV interval may be predetermined and stored in a memory of microcomputer 58, set by the attending physician, determined on the basis of diagnostic data gathered or sensed by IMD 10, external diagnostic means or a physician, and/or determined by comparison to a database or look-up table comprising singular values or ranges of values of max AV intervals that have been determined to be acceptable and that are stored in microcomputer 58. Values for max AV interval may range from 40 ms to 300 ms, and typically is around 180 ms.

At block 102, the activity of the last wait time is checked to see if atrial activity (Asense) has occurred. The activity is most often a FFRW, but any atrial activity may be used, including the atrial activities described above. This avoids signal processing to identify the type of signal. The scheduled ventricular pace time (Vpace_time) is compared to the most recent atrial sense time (Asense_time). If the difference is more than the wait time (Wait_time), the ventricular sense should have been received before the scheduled ventricular pace time, so no fusion beat is expected. A ventricular pace is applied immediately at block 106 and the method ends at block 114.

If the difference between the scheduled ventricular pace time (Vpace_time) and the most recent atrial sense time (Asense_time) is less than the wait time (Wait_time), a fusion beat is still possible so the method proceeds to block 104. The wait time values may be predetermined and stored in a memory of microcomputer 58, set by the attending physician, determined on the basis of diagnostic data gathered or sensed by IMD 10, external diagnostic means or a physician, and/or determined by comparison to a database or look-up table comprising singular values or ranges of values of differences that have been determined to be acceptable and that are stored in microcomputer 58. Values for wait time may range from 0 ms to 30 ms with a typical value is 25 ms.

At block 104, the system waits for a ventricular sense (Vsense) to occur or for an additional wait time (Wait_time) to elapse. If a ventricular sense occurs, the ventricular pace is cancelled at block 108 to avoid a pace leading to a fusion beat. The most recent atrial sense was indeed associated with a later intrinsic ventricular contraction. Because the cancelled ventricular pace would have been a fusion beat, the fusion beat counter at block 110 is incremented. At block 112, the sum in the fusion beat counter is checked against a value N to see if the max AV interval should be increased. Too many fusion beats may indicate that the ventricular pace is being scheduled too early. A longer max AV interval will give the intrinsic rhythm more chance to occur. Intrinsic AV activation is generally preferred to a ventricular paced contraction because it provides improved hemodynamics and extended pacemaker longevity. Pacemaker longevity is increased because fewer paces are required, saving battery energy. Typically, the max AV interval should be increased if three potential fusion beats are detected (N=3), although the value could be as low as 1 or as high as 20, depending on the particular patient. The max AV interval should typically be increased to 220 ms, although it may be increased to a lower value or higher value according to the physician's preference. The max AV interval can also be increased incrementally by a typical value of 50 ms or according to the physician's preference. After the max AV interval has been increased as required, the method ends at block 114. In an alternate embodiment, block 110 and block 112 can be omitted and the max AV interval maintained at its initial value. See FIG. 8.

If the additional wait time (Wait_time) elapses at block 104 without receiving a ventricular sense (Vsense), the method proceeds to block 106 and a ventricular pace (Vpace) is administered. The preceding atrial sense did not indicate an intrinsic ventricular contraction and a ventricular pace is required. After the ventricular pace has been administered, the method ends at block 114.

Figure 8:
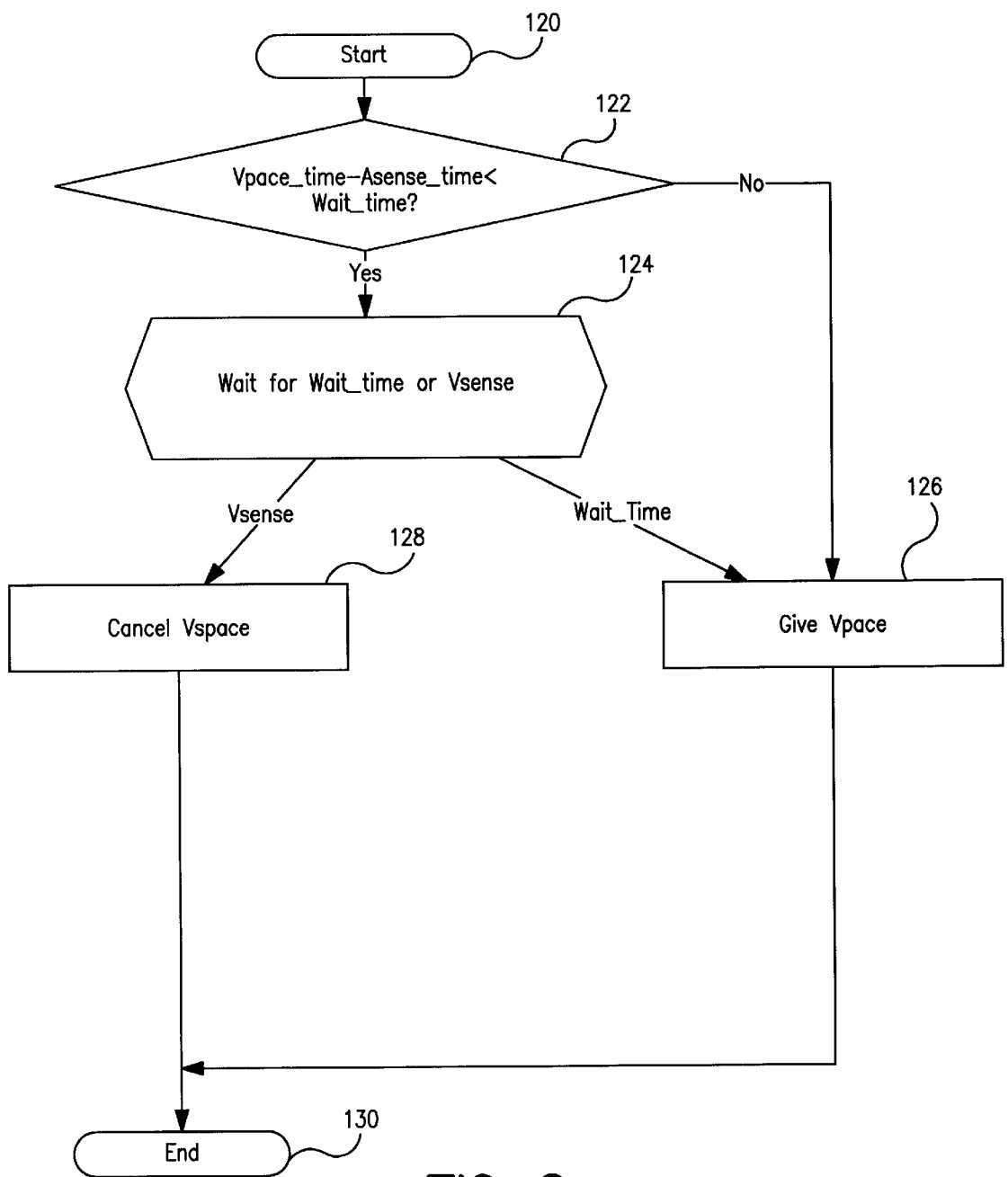
FIG. 8 is a flow chart of another embodiment of a method for ventricular fusion prevention, in accordance with the present invention.

FIG. 8 shows a flow chart of a method for ventricular fusion prevention in accordance with the present invention. An IMD 10 disposed within mammalian heart 8 is programmed to avoid ventricular fusion by using atrial activity to determine if an intrinsic ventricular pulse should be expected. Typically, the atrial activity is a Far Field R-wave (FFRW).

As discussed above, the method of the present invention may be performed under the control of any appropriate computer algorithm stored in a memory or a portion of a memory of microcomputer 58 in IMD 10. Such a computer algorithm may be any program capable of being stored in an electronic medium such as, by way of example only, RAM 68 or ROM 70 of IMD 10, where the contents of RAM 68 and ROM 70 may be accessed and consequently executed by microprocessor 64/microcomputer 58.

Thus an algorithm stored in, for example RAM 68 or ROM 70 of IMD 10 may be used to avoid ventricular fusion. This may be accomplished, for example by using atrial activity, such as FFRW, to determine if an intrinsic ventricular pulse should be expected. The Far Field R-wave (FFRW)

is a product of ventricular depolarization sensed in the atrium by the atrial electrode. The FFRW is normally an unwanted atrial sensed signal and is blanked by the input amplifiers of most current pacemaker systems so that it is not detected. This blanking is unnecessary in the next generation of pacemaker systems, however. The new pacemaker system designs use form parameter analysis based on digital signal processing to discriminating between the various signals. Specific form characteristics of the different signals are analyzed to identify the different signals complexes. Since the blanking window is no longer required, the FFRW can be detected and used to identify ventricular activity, if the analysis can be done fast enough. Other possible atrial activities that may indicate an intrinsic ventricular pulse should be expected are retrograde P-waves and nodal P-waves, originating from the AV node.

In one embodiment of the invention, the electrodes may be placed as shown and described above in FIG. 2. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle. The electrodes serve the dual function of supplying cardiac pacing and sensing cardiac activity. The electrodes can only sense electrical activity near the small tip of the electrode, however. Electric activity may have started in the heart chamber, but not yet have reached the sensing electrode. For example, the tip of the ventricular electrode is typically located in the apex of the right ventricle. The ventricular electric wave front may have left the AV node and be on the way to the apex, but the ventricular electrode will not know that any activity has occurred until the electric wave front reaches the sensing site in the apex.

After an atrial pace or intrinsic atrial contraction, it is reasonable to expect that a ventricular contraction is in progress, even if no ventricular sense has yet occurred. A fusion beat may be avoided by checking to see if an atrial sense has occurred in the prior wait time when a ventricular pace is scheduled, then waiting an additional wait time to see if a ventricular sense takes place if there was an atrial sense (because the atrial sense could be a far field R wave). The "wait time" is defined as a typical time between sensing an intrinsic ventricular contraction at the atrial lead and sensing an intrinsic ventricular contraction at the ventricular lead. The wait time depends on placement of the leads and characteristics of the patient's conduction system, and can vary from −25 ms to 120 ms, with an average value of 60 ms, around a ventricular event. The window of −25 to 0 ms before a ventricular event can be used in this invention. "Far Field R-Wave Classification by Signal Form," by Westendorp et al., PACE, Vol. 22, June 1999, Part II, P218, page A100, reports that FFRWs originating from intrinsic ventricular contractions can be sensed by the atrial lead up to 25 ms before the ventricular contraction has been sensed by the ventricular lead, depending on the position of the atrial lead. The wait time can be selected as a typical value for representing the general population or can be selected to fit a particular patient.

The fusion beat prevention method starts at block 120 of FIG. 8. Typically, the IMD 10 will enter the fusion beat prevention method at the end of the AV delay, that is, when the AV timer has reached the max AV interval and a ventricular pace is scheduled.

As seen in FIG. 6, the max AV interval may be predetermined and stored in a memory of microcomputer 58, set by the attending physician, determined on the basis of diagnostic data gathered or sensed by IMD 10, external diagnostic means or a physician, and/or determined by comparison to a database or look-up table comprising singular values or ranges of values of max AV intervals that have been determined to be acceptable and that are stored in microcomputer 58. Values for max AV interval may range from 40 ms to 300 ms, and typically is around 180 ms.

At block 122, the activity of the last wait time is checked to see if atrial activity (Asense) has occurred. The activity is most often a FFRW, but any atrial activity may be used, including the atrial activities described above. This avoids signal processing to identify the type of signal. The scheduled ventricular pace time (Vpace_time) is compared to the most recent atrial sense time (Asense_time). If the difference is more than the wait time (Wait_time), the ventricular sense should have been received before the scheduled ventricular pace time, so no fusion beat is expected. A ventricular pace is applied immediately at block 126 and the method ends at block 130.

If the difference between the scheduled ventricular pace time (Vpace_time) and the most recent atrial sense time (Asense_time) is less than the wait time (Wait_time), a fusion beat is still possible so the method proceeds to block 124. The wait time values may be predetermined and stored in a memory of microcomputer 58, set by the attending physician, determined on the basis of diagnostic data gathered or sensed by IMD 10, external diagnostic means or a physician, and/or determined by comparison to a database or look-up table comprising singular values or ranges of values of differences that have been determined to be acceptable and that are stored in microcomputer 58. Values for wait time may range from 0 ms to 30 ms with a typical value is 25 ms.

At block 124, the system waits for a ventricular sense (Vsense) to occur or for an additional wait time (Wait_time) to elapse. If a ventricular sense occurs, the ventricular pace is cancelled at block 128 to avoid a pace leading to a fusion beat. The most recent atrial sense was indeed associated with a later intrinsic ventricular contraction and the method ends at block 130.

If the additional wait time (Wait_time) elapses at block 124 without receiving a ventricular sense (Vsense), the method proceeds to block 126 and a ventricular pace (Vpace) is administered. The preceding atrial sense did not indicate an intrinsic ventricular contraction and a ventricular pace is required. After the ventricular pace has been administered, the method ends at block 130.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to a method of ventricular fusion prevention. The present invention is also not limited to ventricular fusion prevention algorithms per se, but may find further application as a means for preventing ventricular fusion. The present invention further includes within its scope methods and systems for ventricular fusion prevention described above.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

We claim:

1. A method for ventricular fusion prevention, comprising:

providing a value for wait time, scheduling a ventricular pace;

determining whether an atrial sense occurred within the wait time;

administering the scheduled ventricular pace if no atrial sense occurred within the wait time;

awaiting either a ventricular sense or an additional wait time, if an atrial sense occurred within the wait time;

canceling the ventricular pace if the ventricular sense occurs; and administering the scheduled ventricular pace if the additional wait time passes.

2. The method of claim 1, wherein an individual patient determines the wait time by testing.

3. The method of claim 1, wherein the wait time is in the range of 0 to 30 ms.

4. The method of claim 1, wherein the wait time is selected from the ranges consisting of 10 ms to 30 ms, 20 ms to 30 ms, and 23 ms to 27 ms.

5. The method of claim 1, wherein the wait time is 25 ms.

6. The method of claim 1, further comprising:

providing a max AV interval;

incrementing a fusion beat counter if the ventricular pace is canceled; and increasing the max AV interval if the fusion beat counter exceeds a predetermined value.

7. The method of claim 6, wherein an individual patient determines the value of the fusion beat counter by testing.

8. The method of claim 6, wherein the value of the fusion beat counter is from 1 to 20.

9. The method of claim 6, wherein the fusion beat counter value is selected from the ranges consisting of 1 to 20, 1 to 10, and 1 to 5.

10. The method of claim 6, wherein the value of the fusion beat counter is 3.

11. The method of claim 6, wherein the physician for an individual patient determines the value of the max AV interval increase.

12. The method of claim 6, wherein the value of the max AV interval is increased by 50 ms.

13. The method of claim 6, wherein the physician for an individual patient determines an amount to increase the value of the max AV interval.

14. The method of claim 6, wherein the value of the max AV interval is increased to 220 ms.

15. An implantable medical system with ventricular fusion prevention, comprising:

means for providing a value for wait time, means for scheduling a ventricular pace;

means for determining whether an atrial sense occurred within the wait time;

means for administering the scheduled ventricular pace if no atrial sense occurred within the wait time;

means for awaiting either a ventricular sense or an additional wait time, if an atrial sense occurred within the wait time;

means for canceling the ventricular pace if the ventricular sense occurs; and means for administering the scheduled ventricular pace if the additional wait time passes.

16. The system of claim 15, wherein the wait time is in the range of 0 to 30 ms.

17. The method of claim 15, wherein the wait time is selected from the ranges consisting of 10 ms to 30 ms, 20 ms to 30 ms, and 23 ms to 27 ms.

18. The method of claim 15, wherein the wait time is 25 ms.

19. The system of claim 15, further comprising:

means for providing a max AV interval;

means for incrementing a fusion beat counter if the ventricular pace is canceled; and means for increasing the max AV interval if the fusion beat counter exceeds a predetermined value.

20. The system of claim 19, wherein the value of the fusion beat counter is from 1 to 20.

21. The method of claim 19, wherein the value of the fusion beat counter is selected from the ranges consisting of 1 to 20, 1 to 10, and 1 to 5.

22. The system of claim 19, wherein the value of the fusion beat counter is 3.

23. The system of claim 19, wherein the value of the max AV interval is increased by 50 ms.

24. The system of claim 19, wherein the value of the max AV interval is increased to 220 ms.

25. A computer usable medium storing computer readable program code having a program for ventricular fusion prevention, comprising:

computer readable program code that provides a value for wait time, computer readable program code that schedules a ventricular pace;

computer readable program code that determines whether an atrial sense occurred within the wait time;

computer readable program code that administers the scheduled ventricular pace if no atrial sense occurred within the wait time;

computer readable program code that awaits either a ventricular sense or an additional wait time, if an atrial sense occurred within the wait time;

computer readable program code that cancels the ventricular pace if the ventricular sense occurs; and computer readable program code that administers the scheduled ventricular pace if the additional wait time passes.

26. The program of claim 25, wherein the wait time is in the range of 0 to 30 ms.

27. The method of claim 25, wherein the wait time is selected from the ranges consisting of 10 ms to 30 ms, 20 ms to 30 ms, and 23 ms to 27 ms.

28. The method of claim 25, wherein the wait time is 25 ms.

29. The program of claim 25, further comprising:

computer readable program code that provides a max AV interval;

computer readable program code that increments a fusion beat counter if the ventricular pace is canceled; and computer readable program code that increases the max AV interval if the fusion beat counter exceeds a predetermined value.

30. The program of claim 29, wherein the value of the fusion beat counter is from 1 to 20.

31. The method of claim 29, wherein the value of the fusion beat counter is selected from the ranges consisting of 1 to 20, 1 to 10, and 1 to 5.

32. The program of claim 29, wherein the value of the fusion beat counter is 3.

33. The program of claim 29, wherein the value of the max AV interval is increased by 50 ms.

34. The program of claim 29, wherein the value of the max AV interval is increased to 220 ms.

* * * * *